US00PP33795P2

(12) United States Plant Patent
Hansen

(10) Patent No.: US PP33,795 P2
(45) Date of Patent: Dec. 28, 2021

(54) ***PHLOX* PLANT NAMED 'MAGENTA PEARL'**

(50) Latin Name: ***Phlox* hybrid**
Varietal Denomination: Magenta Pearl

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,431

(22) Filed: Jun. 29, 2021

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 5/02
See application file for complete search history.

*Primary Examiner* — Kent L Bell

(57) ABSTRACT

A new and unique cultivar of garden *Phlox* named *Phlox* plant 'Magenta Pearl' multi-stemmed, short, upright, slowly-spreading habit with clean green, glossy, lanceolate leaves with exceptional powdery mildew resistance. Foliage is thick on stiff, upright stems. Faint to lightly sweet fragrant flowers of deep magenta-pink faces with light pink halo and darker eye zones midribs are produced on multiple branched peduncles and cover the top of the plant beginning early summer about two weeks prior typical *Phlox paniculata* cultivars. 'Magenta Pearl' is especially suitable as a potted plant, for the garden, for attracting hummingbirds and butterflies, and for cut flower arrangements.

1 Drawing Sheet

Botanical classification: *Phlox* hybrid.
Variety denomination: 'Magenta Pearl'.

STATEMENT REGARDING PRIOR DISCLOSURES UNDER 37 CFR 1.77(B)(6)

The first non-enabling disclosure of the claimed plant, in the form of a photograph and brief description on a website operated by Walters Gardens, Inc. on Feb. 1, 2020. Subsequently, the new plant was advertised in the "Walters Gardens 20-21 Catalog" by Walters Gardens, Inc. released on May 20, 2020. The claimed plant was first sold to the public on Jul. 13, 2020 by Walters Gardens, Inc., who obtained the plant and all information relating thereto, from the inventor. No plants of *Phlox* 'Magenta Pearl' have been sold to the public in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Phlox* plant, known as *Phlox* 'Magenta Pearl' and will be referred to hereafter by its cultivar name or the "new plant". The new plant was the result of a cross of *Phlox* 'Amethyst Pearl' U.S. Plant Pat. No. 28,487 as the female or seed parent times the male or pollen parent *Phlox carolina* 'Lil' Cahaba' (not patented) performed at a wholesale perennial nursery in Zeeland, Mich. Nov. 17, 2014. The new plant was initially given the breeder code 14-24-3 throughout subsequent evaluations at the same nursery. 'Magenta Pearl' has been asexually propagated by stem cuttings in the greenhouses at the same nursery in Zeeland, Mich. since 2016. The unique characteristics of the new plant have been found to be reproducible and stable in successive generations of asexually propagated plants and the resultant plants have been found to be identical to the original selection.

BRIEF SUMMARY OF THE PLANT

*Phlox* 'Magenta Pearl' is unique from its parents and all other tall garden *Phlox* or other *Phlox* known to the inventor. The new plant differs from the female parent 'Amethyst Pearl' in that the female parent has a slightly shorter habit with light amethyst-colored flowers. The male parent is shorter in habit with narrower foliage and deeper magenta flowers.

The closest comparison cultivars known to the inventor are 'Fashionable Early Flamingo' U.S. Plant Pat. No. 29,911, 'Fashionable Early Princess' U.S. Plant Pat. No. 28,680, 'Kung Fuchsia' U.S. Plant Pat. No. 31,308, 'Forever Pink' U.S. Plant Pat. No. 24,918, 'Opening Act Ultrapink' U.S. Plant Pat. No. 32,093 and 'Minnie Pearl' (not patented). 'Fashionable Early Flamingo' has a taller and broader habit and flowers of light lavender-pink. 'Fashionable Early Princess' has a larger, broader and taller habit with flowers of light fuchsia-pink. 'Forever Pink' is shorter in habit and lighter pink in flower color. 'Kung Fuchsia' has a shorter habit with flowers of intense, bright, fuchsia-pink. 'Opening Act Ultrapink' has slightly lighter pink flowers of fluorescent rose-pink and the flower is slightly larger with a wider face. 'Minnie Pearl' has a slightly shorter habit and flowers of pure white.

'Magenta Pearl' is distinct from all other *Phlox* known to the inventor in the following repeatedly-observed combination of traits:

1. Plants of medium upright habit, slowly spreading by short rhizomes, producing clean, glossy, clean green, lanceolate leaves;

2. Showing exceptional powdery mildew resistance;
3. Multiple branched, stems produce rounded mounds of early flowers;
4. Faint to lightly sweet fragrant flowers on strong stiff stems of about 47.0 cm tall producing deep magenta-pink flower faces with light pink halo and darker eye zones midrib markings;
5. Flowers cover the entire top of the plant;
6. Flowering beginning in early-summer about two weeks prior to typical *Phlox paniculata* cultivars and re-blooming through late-summer.

BRIEF DESCRIPTION OF THE DRAWINGS

The photographs of the new plant demonstrate the unique traits of 'Magenta Pearl' and the overall appearance of the plant at three-years-old grown in a full sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
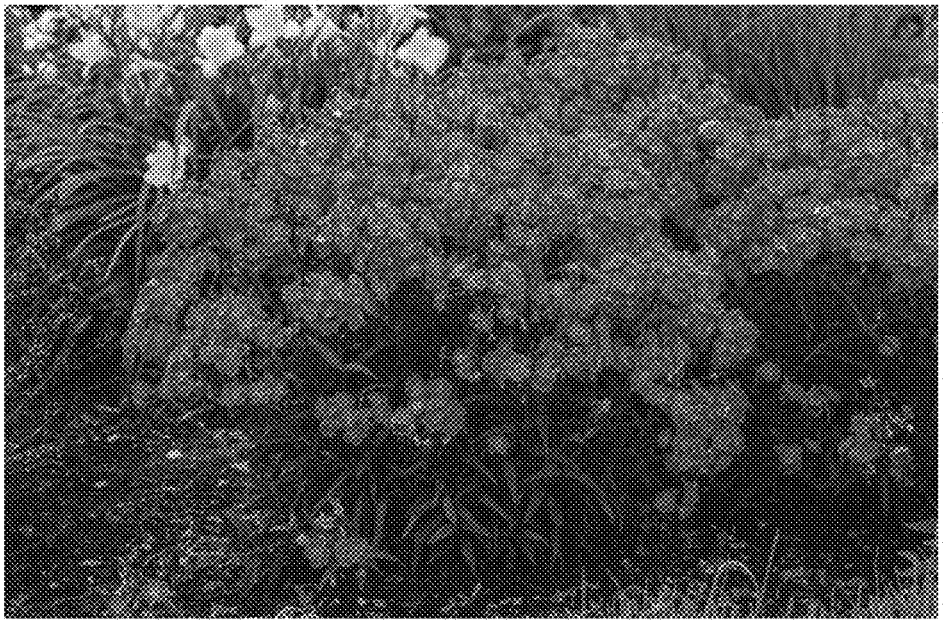
FIG. 1 shows the new plant in peak flower in the landscape.
Figure 2:
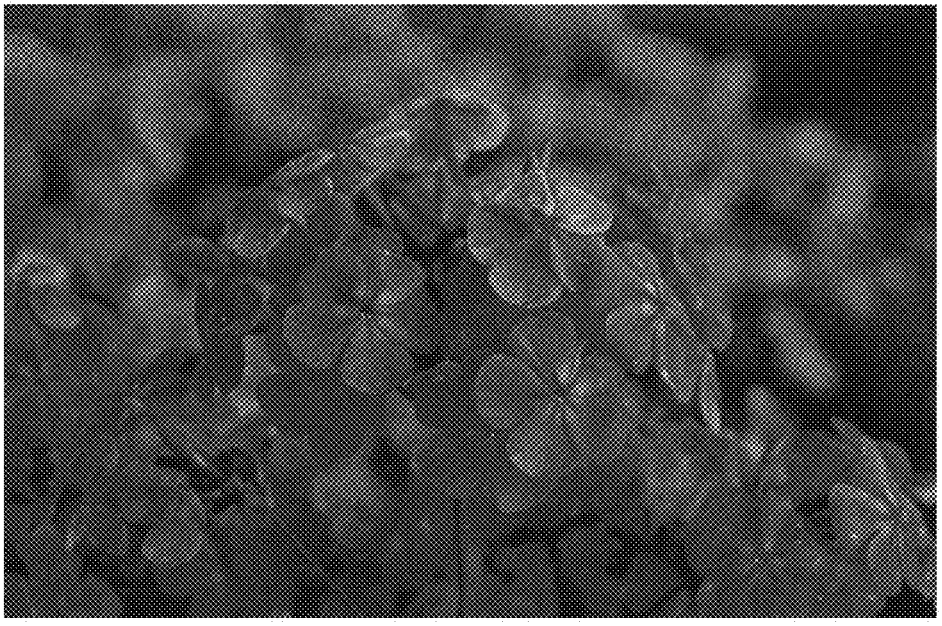
FIG. 2 shows a close-up of the floriferous flower head with flowers.

The following descriptions and color references are based on the 2015 edition of The Royal Horticultural Society Colour Chart except where common dictionary terms are used. *Phlox* 'Magenta Pearl' has not been observed under all possible environments. The phenotype may vary slightly with different growing environments such as temperature, light, fertility, soil pH, moisture and maturity levels, but without any change in the genotype. The following observations and size descriptions are based on two to four-year-old plants in the full sun trial garden of a wholesale perennial nursery in Zeeland, Mich. with supplemental fertilizer and water as needed.

Botanical classification: *Phlox* hybrid;

Parentage: Female or seed parent was *Phlox* 'Amethyst Pearl'; male or pollen parent was 'Lil' Cahaba';

Plant habit: Hardy herbaceous perennial, densely upright, producing about 22 rigid upright stems; flowering to about 47 cm tall and about 107 cm wide; flowering begins early summer in Michigan and continuing for about 5 weeks with rebloom if deadheaded;

Propagation: Stem cuttings; rooting in about 14 days;

Time to produce finished crop in 3.8 liter pots: About 8 to 10 weeks; moderate rate of growth;

Root: Primary roots to about 1.0 mm thick; secondary fibrous and freely branching; color creamy-white to tan depending on soil type;

Leaves: Simple; opposite to subopposite; narrowly lanceolate; entire margin; narrowly acute apex; rounded to attenuate base;

Leaf size: To about 106.0 mm long by about 15.0 mm wide, average about 95.0 mm long by about 13.0 mm wide;

Leaf surfaces: Lustrous adaxial and matte abaxial; glabrous adaxial and abaxial;

Leaf color expanding: Adaxial between RHS 146B and RHS 144A, abaxial nearest RHS 146D;

Leaf color at flowering: Adaxial nearest RHS 137A, abaxial nearest RHS 147C;

Foliage fragrance: None detected;

Veins: Pinnate; glabrous abaxial and adaxial; midrib about 1.0 mm wide at base, slightly sunken adaxial and raised abaxial; secondary veins indistinguishable;

Vein color: Adaxial midrib nearest RHS 151C, abaxial midrib nearest RHS 146D; other adaxial and abaxial veins same color as surrounding leaf;

Petiole: Leaves sessile;

Stems: Cylindrical; stiff; wiry; strong; upright; glabrous; to about 45 cm long and 5 mm diameter at base, average about 42 cm long and 3.5 mm diameter at base;

Stem color: Proximal lowest two internode segments nearest RHS 187C with undertone of nearest RHS 146C; distally between RHS 146D and RHS 145A;

Nodes: About 9 per stem below flowers; average internode length about 3.3 cm;

Node color: Between RHS 146D and RHS 145A;

Inflorescence: A loosely-branched compound corymb of about 100 to 200 flowers; to about 13.5 cm tall and 23.0 cm across;

Flowers: Perfect; salverform with flat face and long fused tube; actinomophic; typically with five petals; about 27.0 mm long total with tube about 26.0 mm long; face about 25.0 mm across; attitude upright to outward;

Flower longevity: About 5 days on plant or as cut flower; self-cleaning;

Flower fragrance: Faint to lightly sweet;

Buds one to two days prior to opening: Narrowly oblanceolate, to nearly clavate; acute apex with convolute petals; base fused into corolla tube; about 25.0 mm long in total, tube portion about 15 mm long and 2.0 mm diameter, and swollen bulb portion about 10.0 mm long and 3.5 mm diameter toward base of convolute petals;

Bud color: Corolla tube nearest RHS N81C and bulb between RHS N81B and RHS 77A;

Petals: Five; margin entire; apex truncate to rounded; base fused into tube; abaxial and adaxial limb and tube glabrous except pubescent in adaxial region about 5.0 mm to 7.0 mm from base; limb imbricate about 25% over next petal;

Petal size: Basal 24.0 mm fused into tube, to a diameter of about 3.0 mm; limbs about 12.5 mm across, and about 12.5 mm long; imbricate about 3.1 mm of the petals to either side;

Petal color: Young adaxial limb distal portion between RHS N80A and RHS N78B, proximal midrib nearest N78A, with surrounding center eye portion nearest RHS 77D; young abaxial limb between N78B and RHS N78C with center eye nearest RHS 76D; young adaxial tube base nearest RHS 145D and mid and distal region nearest RHS 76D; young abaxial tube base nearest RHS 145D and mid and distal region nearest RHS N79D with veins nearest N79C; mature adaxial limb nearest RHS N74C with proximal midrib nearest RHS NN78D; mature abaxial limb nearest RHS N75D; mature adaxial tube base nearest RHS NN155B and mid and distal portion nearest RHS N79D; mature abaxial tube base nearest RHS NN155B and mid and distal portion nearest RHS N79D;

Androecium:

*Filaments*.—Typically five; adnate to adaxial petals except free in terminal 1.0 mm; varying lengths between 17.0 mm and 22.0 mm, less than 0.5 mm in diameter; white, nearest RHS 76C.

*Anther*.—Five; oblong elliptic; dorsifixed; longitudinal; about 3.5 mm long by 1.0 mm wide; color nearest RHS 14B.

*Pollen*.—Abundant; color nearest RHS 17A.

Gynoecium: One pistil per flower; to about 22.0 mm long;

*Style*.—Cylindrical; about 20.0 mm long and less than 0.3 mm diameter; color base nearest RHS 145D, distal section nearest RHS 64B.

*Stigma*.—Trifurcate in the distal 1.0 mm, less than 0.25 mm in diameter; persistent after flower abscission; color nearest RHS 13B.

*Ovary*.—Superior; conical; about 1.5 mm long and 1.0 mm diameter; color nearest RHS 145A.

Calyx: Tubular; to about 7.0 mm long and 3.0 mm wide at apex;

Sepals: Five; lanceolate; narrowly acute apex, margin entire; base fused; glabrous and lustrous adaxial and abaxial; individually about 7.0 mm long and 1.5 mm wide; fused in basal 4.0 mm;

Sepal color: Adaxial center nearest RHS 137B, margin of fused portion nearest RHS 186D, distal margin nearest RHS NN155C; abaxial fused margins nearest RHS 186D in high light and nearest RHS NN155C in low light, apex nearest RHS 147B, proximally highly blushed to solid RHS 187C in high light and nearest RHS 145A;

Peduncle: Cylindrical; glabrescent to glabrous; lustrous; stiff; strong; upright; about 45.0 cm long and 3.0 mm diameter at base of flower branches; branches micro puberulent, to about 14.5 cm long and 2.0 mm diameter at base, to about 45° angle above horizontal;

Peduncle color: Between RHS 146D and RHS 145A;

Branch color: Between RHS 146D and RHS 145A with slight anthocyanin blush of nearest RHS 187C;

Pedicel: Terete; micro puberulent; to about 3.0 mm long and 0.7 mm diameter; mostly outwardly;

Pedicel color: Between RHS 146D and RHS 145A with slight anthocyanin blush of nearest RHS 187C, developing to heavy blush of nearest RHS 187C after flower abscission;

Fruit and seeds: Have not yet been observed;

Hardiness and culture: The new plant grows best with plenty of moisture and adequate drainage; hardy to at least from USDA zone 5 through 8.

Disease and pest resistance: *Phlox* 'Magenta Pearl' demonstrated the excellent powdery mildew resistance caused by *Erysiphe cichoracearum* under conditions of intense pressure that would normally show symptoms.

I claim:

1. A new and distinct cultivar of hybrid *Phlox* plant named *Phlox* 'Magenta Pearl' as herein described and illustrated.

* * * * *